(12) United States Patent
Sörnmo et al.

(10) Patent No.: US 8,287,725 B2
(45) Date of Patent: Oct. 16, 2012

(54) PREDICTION OF RAPID SYMPTOMATIC BLOOD PRESSURE DECREASE

(75) Inventors: Leif Sörnmo, Lund (SE); Kristian Solem, Malmö (SE); Bo Olde, Lund (SE)

(73) Assignee: Gambro Lundia AB (SE)

( * ) Notice: Subject to any disclaimer, the term of this patent is extended or adjusted under 35 U.S.C. 154(b) by 818 days.

(21) Appl. No.: 12/308,052

(22) PCT Filed: Jun. 4, 2007

(86) PCT No.: PCT/EP2007/055477
§ 371 (c)(1),
(2), (4) Date: Dec. 5, 2008

(87) PCT Pub. No.: WO2007/141246
PCT Pub. Date: Dec. 13, 2007

(65) Prior Publication Data
US 2009/0272678 A1    Nov. 5, 2009

Related U.S. Application Data

(60) Provisional application No. 60/804,109, filed on Jun. 7, 2006, provisional application No. 60/826,482, filed on Sep. 21, 2006.

(30) Foreign Application Priority Data

Sep. 19, 2006    (SE) ...................................... 0601929

(51) Int. Cl.
*B01D 61/12* (2006.01)
*A61B 5/024* (2006.01)

(52) U.S. Cl. ............ 210/85; 210/90; 210/646; 600/323; 600/324; 600/483; 600/502; 604/65; 700/273; 702/19; 702/189

(58) Field of Classification Search .................... 210/90, 210/143, 321.6, 646, 741, 85, 739; 600/323, 600/324, 481–507, 322, 547; 604/5.01, 6.01, 604/65; 700/12, 14, 273; 702/189–194, 702/19; 708/422
See application file for complete search history.

(56) References Cited

U.S. PATENT DOCUMENTS 3,871,362 A    3/1975    Dunegan
(Continued)

FOREIGN PATENT DOCUMENTS

EP    1 155 659 A1    11/2001
(Continued)

OTHER PUBLICATIONS

B. Agroyannis, et al., "Telemedicine technology and applications for home hemodialysis", The International Journal of Artificial Organs, vol. 22, No. 10, pp. 679-683 (1999).

*Primary Examiner* — Joseph Drodge
(74) *Attorney, Agent, or Firm* — Finnegan, Henderson, Farabow, Garrett & Dunner LLP

(57) ABSTRACT

The invention relates to prediction of a rapid symptomatic drop in a subject's blood pressure, e.g. during a medical treatment or when operating an aircraft. To this aim, a pulse shape parameter (Pps) with respect to a peripheral body part (105) of the subject (P) is registered by means of a pulse oximetry instrument (110) adapted to detect light response variations in blood vessels. An initial pulse magnitude measure is calculated based on a pulse shape parameter (Pps) received at a first instance. During a measurement period subsequent to the first instance, a respective pulse magnitude measure is calculated based on each of a number of received pulse shape parameters (Pps). It is further investigated, for each pulse magnitude measure in the measurement period, whether or not the measure fulfills a decision criterion relative to the initial pulse magnitude measure. An alarm triggering signal (α) is generated if the decision criterion is found to be fulfilled.

24 Claims, 5 Drawing Sheets

U.S. PATENT DOCUMENTS

| | | | |
|---|---|---|---|
| 4,710,164 A | 12/1987 | Levin et al. | |
| 4,807,630 A * | 2/1989 | Malinouskas | 600/323 |
| 4,819,646 A * | 4/1989 | Cheung et al. | 600/323 |
| 4,828,543 A * | 5/1989 | Weiss et al. | 604/6.09 |
| 4,950,395 A * | 8/1990 | Richalley | 210/195.2 |
| 6,397,092 B1 * | 5/2002 | Norris et al. | 600/323 |
| 6,430,525 B1 * | 8/2002 | Weber et al. | 702/194 |
| 6,736,789 B1 | 5/2004 | Spickermann | |
| 6,804,002 B2 * | 10/2004 | Fine et al. | 356/364 |
| 6,822,564 B2 * | 11/2004 | Al-Ali | 340/511 |
| 6,918,879 B2 * | 7/2005 | Ting et al. | 600/485 |
| 7,004,907 B2 * | 2/2006 | Banet et al. | 600/485 |
| 7,668,579 B2 * | 2/2010 | Lynn | 600/323 |
| 2003/0137423 A1 | 7/2003 | Al-Ali | |
| 2003/0212316 A1 | 11/2003 | Leiden et al. | |
| 2005/0148882 A1 * | 7/2005 | Banet et al. | 600/485 |
| 2005/0228296 A1 | 10/2005 | Banet | |
| 2005/0228301 A1 | 10/2005 | Banet et al. | |
| 2005/0261594 A1 | 11/2005 | Banet | |
| 2006/0142648 A1 * | 6/2006 | Banet et al. | 600/300 |
| 2008/0067132 A1 | 3/2008 | Ross et al. | |

FOREIGN PATENT DOCUMENTS

| | | |
|---|---|---|
| GB | 1 426 319 | 2/1976 |
| JP | 2-147047 | 6/1990 |
| JP | 8-000583 | 1/1996 |
| WO | WO 2006/031186 A1 | 3/2006 |

* cited by examiner

PREDICTION OF RAPID SYMPTOMATIC BLOOD PRESSURE DECREASE

CROSS REFERENCE TO RELATED APPLICATIONS

This application is a national phase application based on PCT/EP2007/055477, filed Jun. 4, 2007, which claims the priority of Swedish Patent Application No. 0601929-3, filed Sep. 19, 2006; and claims the benefit of U.S. Provisional Application Nos. 60/804,109, filed Jun. 7, 2006, and 60/826,482, filed Sep. 21, 2006, the contents of all of which are incorporated herein by reference.

THE BACKGROUND OF THE INVENTION AND PRIOR ART

The present invention relates generally to detection of the onset of rapid (acute) symptomatic drop in a subject's blood pressure. More particularly, the invention relates to an alarm apparatus, a medical system, a method, a computer program, and a computer readable medium.

There exist many situations wherein it is important to detect potential hypotension, and if possible avoid the actual occurrence thereof, for example when performing artificial blood purification. The human body consists of approximately 60% water—a level which is important to maintain for survival. While it is unproblematic to provide the body with new water, disposal of surplus water is a major problem in renal patients. The task of the normal kidney is to remove superfluous fluid from the blood, such as water, urea and other waste products. The resulting urine is transferred to the bladder and finally leaves the body during urination. The kidney's second task is to regulate for example the balance of acid and base. With malfunctioning kidneys, disorders may develop in most major body organs, a syndrome called uremia. If uremia remains untreated, it will lead to death. Uremia is treated either by kidney transplantation, or some kind of blood treatment, extracorporeal or intracorporeal.

During an artificial blood purification process, such as extracorporeal blood treatment, it is common that the patient suffers from symptomatic hypotension, characterized by a blood pressure drop with symptoms in the form of cramps, nausea, vomiting and sometimes fainting. Such an event is not only strenuous for the patient, but also requires considerable attention from the staff overseeing the treatment. Consequently, during such blood treatment, it is highly desirable to detect the onset of symptomatic hypotension and preventing it from coming about.

However, there are other examples of situations in which it is vital to predict, and if possible prevent, rapid symptomatic hypotension. For instance fighter plane pilots are often subjected to forces that risk result in that the pilot faints. However, also operators of other types of vehicles, crafts and machines may need similar surveillance in order to reduce hazards to the operators, other people and various material goods.

The published US patent application 2004/0254473 describes a laser blood-flow meter and a system for monitoring bio-data of a person. The laser blood-flow meter measures a respective blood flow in different quarters of a biological structure by irradiating laser beams to the structure and detecting resulting scattered beams. Based on the detected light, it is then judged whether the person to which the biological structure belongs is in a serious condition. For example, this judgement may be based on a reduction in blood flow relative to previously recorded standards, reduction in an amplitude of a blood-flow waveform relative to the standards, and a heartbeat frequency increase.

However, there is yet no solution, which on one hand, provides a quick and reliable hypotension warning, and on the other hand, is cost-efficient and straightforward to implement.

SUMMARY OF THE INVENTION

The object of the present invention is therefore to alleviate the problem above and thus accomplish an uncomplicated solution by means of which the onset of acute symptomatic blood pressure decrease can be detected at a point in time when any effects thereof, still may be avoided.

According to one aspect of the invention, the object is achieved by the initially described alarm apparatus, wherein the pulse recording means includes a pulse oximetry instrument adapted to register the pulse shape parameter based on light response variations in at least one blood vessel of the subject. The control unit further includes a processing unit, which is adapted to calculate an initial pulse magnitude measure based on a pulse shape parameter received at a first instance, and to store the initial pulse magnitude measure in a memory means associated with the control unit. During a measurement period subsequent to the first instance, the processing unit is adapted to calculate a respective pulse magnitude measure based on each of a number of received pulse shape parameters. Moreover, for each pulse magnitude measure in the measurement period, the processing unit is adapted to investigate whether or not the measure fulfills a decision criterion relative to the initial pulse magnitude measure. If such a criterion is found to be fulfilled, the processing unit is adapted to generate an alarm triggering signal. Thus, appropriate measures can be taken, automatically and/or manually, to avoid (or at least reduce the risk) that hypotension is coming about.

An important advantage by this design is that an early hypotension warning can be provided based on comparatively small processing resources and sensors being simple and cost-efficient. Moreover, the sensors used are recognized within medicine, and have a well-established functionality.

According to a preferred embodiment of this aspect of the invention, the processing unit is adapted to regard the decision criterion as fulfilled if: an examined pulse magnitude measure of a given pulse shape parameter is below a threshold value calculated based on the initial pulse magnitude measure; and a predetermined amount (say 50-100%) of the pulse magnitude measures of the pulse shape parameters received within a test period after the given pulse shape parameter are below the threshold value.

Preferably, the test period is an interval selected from a range extending from approximately three minutes to approximately fifteen minutes, and more preferably the test period is approximately five minutes long. Thus, depending on the threshold value, the predetermined amount of pulse magnitude measures required to fulfill the decision criterion and the test period length selected, a robust and reliable hypotension warning can be obtained for a large variety of subjects and applications.

According to another preferred embodiment of this aspect of the invention, the processing unit is adapted to calculate the threshold value by normalizing the intitial pulse magnitude measure, and dividing the normalized initial pulse magnitude measure by a predefined denominator, for instance a value selected from a range from approximately 1.2 to approximately 5. Hence, by selecting the threshold value, the algorithm can be calibrated regarding the length of the test period to attain a desired balance between early warning and false alarms. Generally, however, a relatively large denominator requires a comparatively short test period, and vice versa.

According to yet another preferred embodiment of this aspect of the invention, the processing unit is adapted to, during the measurement period, calculate a pulse magnitude measure for any received pulse shape parameter by dividing an original measure with the initial pulse magnitude measure representing the normalized initial pulse magnitude measure having been divided by the predefined denominator. Hence, an unbiased comparison with the initial status can be made.

According to a further preferred embodiment of this aspect of the invention, the arrangement includes an auxiliary recording means, which is adapted to repeatedly register a bio-impedance parameter representing a degree of contraction of the subject's capillary blood vessels. Moreover, the processing-unit is adapted to receive the bio-impedance parameter and investigate whether or not the bio-impedance parameter fulfills an auxiliary alarm criterion. Also upon fulfillment of this criterion, the processing unit is adapted to generate the alarm triggering signal. Hence, a complementary hypotension detection means is provided, and thereby a more reliable function.

According to another preferred embodiment of this aspect of the invention, the arrangement is adapted to predict rapid symptomatic blood pressure decrease in a subject undergoing blood treatment. Here, the processing unit is adapted to calculate the initial pulse magnitude measure based on a pulse shape parameter received during an initial phase of the blood treatment. Thus, the hypotension detection is based on a reference value being relatively unaffected by the treatment. This further enhances the reliability.

According to another aspect of the invention, the object is achieved by a medical system adapted to perform blood treatment of a subject. In addition to the above-proposed alarm arrangement, the system includes a dialysis machine adapted to perform extracorporeal blood treatment of a subject. Hence, blood treatment and hypotension surveillance can be effected in parallel in a straightforward manner.

According to another aspect of the invention the object is achieved by the initially described method, wherein the registering of the pulse shape parameter involves a pulse oximetry measurement. Thereby, the pulse shape parameter is determined based on light response variations in at least one blood vessel of the subject. Moreover, the method includes calculating an initial pulse magnitude measure based on a pulse shape parameter received at a first instance, and storing the initial pulse magnitude measure in a memory means. During a measurement period subsequent to the first instance, a respective pulse magnitude measure is calculated based on each of a number of received pulse shape parameters. For each pulse magnitude measure in the measurement period it is investigated whether or not the measure fulfills a decision criterion relative to the initial pulse magnitude measure, and if so, an alarm triggering signal is generated.

The advantages of this method, as well as the preferred embodiments thereof, are apparent from the discussion hereinabove with reference to the proposed alarm apparatus.

According to a further aspect of the invention the object is achieved by a computer program directly loadable into the internal memory of a computer, comprising software for controlling the above proposed method when said program is run on a computer.

According to another aspect of the invention the object is achieved by a computer readable medium, having a program recorded thereon, where the program is to make a computer control the above proposed method.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

DESCRIPTION OF PREFERRED EMBODIMENTS OF THE INVENTION

Figure 1:
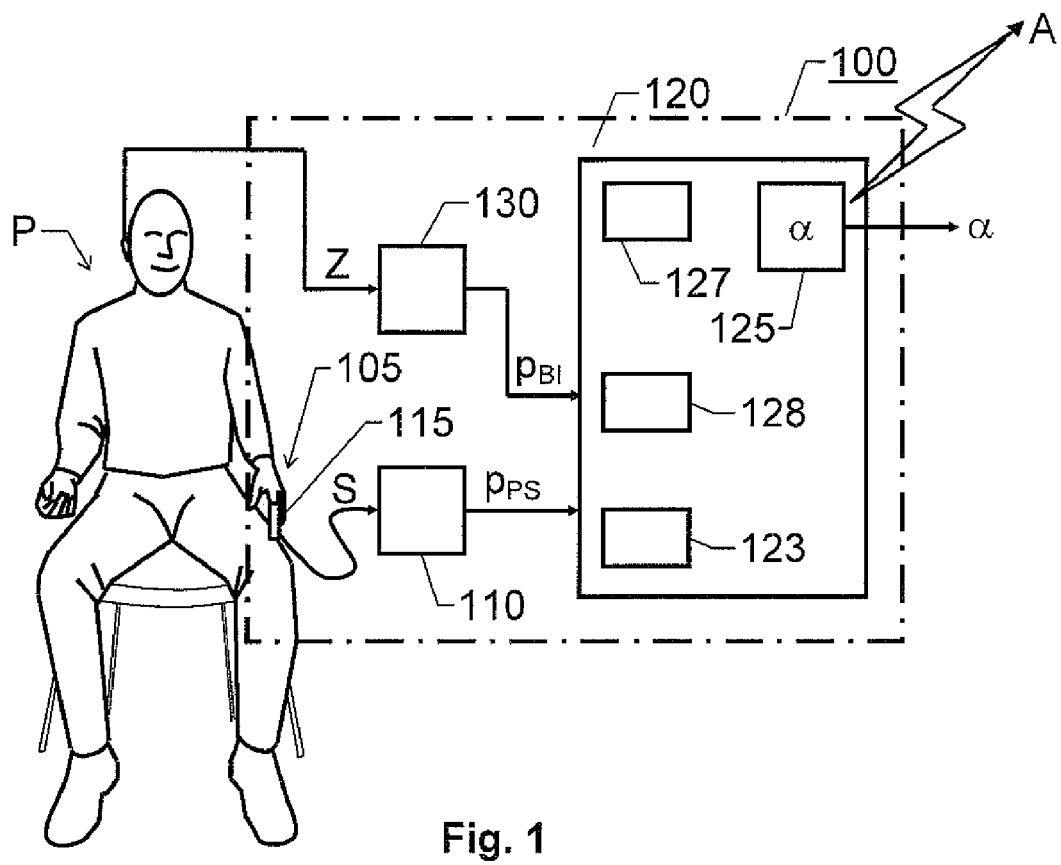
FIG. 1 shows a schematic image of an alarm arrangement according to one embodiment of the invention.

We refer initially to FIG. 1, which depicts an alarm arrangement 100 for predicting rapid symptomatic blood pressure decrease in a subject P according to one embodiment of the invention. The arrangement 100 includes a pulse recording means 110 and 115 respectively, and a control unit 120.

The pulse recording means has a pulse oximetry instrument 110, and preferably a separate sensor unit 115. This unit 115 includes at least one light source and at least one light detector through which a pulse signal S is registered that describes light response variations in at least one blood vessel in a peripheral body part 105 of the subject P (e.g. in a finger, a toe, an earlobe, a nose tip or other extremity, in the skin thereof, or in the skin of any other body part) depending on where the sensor unit 115 is attached to the subject P. The light response variations preferably reflect variations in the absorption of the light transmitted from said at least one light source. However, light reflectance and/or light transmittance may equally well be studied. In any case, the pulse oximetry instrument 110 is adapted to register a pulse shape parameter $p_{PS}$ based on the pulse signal S.

The control unit 120 is adapted to receive and process the pulse shape parameter $p_{PS}$. Specifically, the control unit 120 includes a processing unit 128, which is adapted to store a pulse shape parameter $p_{PS}$ received at a first instance $t_1$ in a memory means 123. The memory means 123 is either included in the control unit 120, or associated thereto, e.g. via a cable or a wireless connection. In any case, the processing unit 128 is adapted to calculate an initial pulse magnitude measure PM1 based on the value stored in the memory means 123.

Figure 3A:
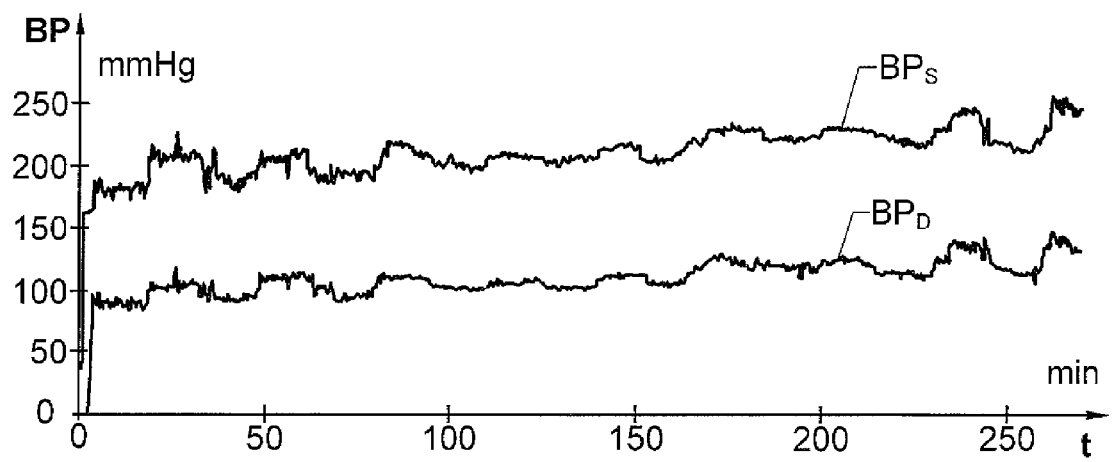
FIG. 3a shows a graph illustrating an example of a first subject's blood pressure variation during a blood treatment process.
Figure 3B:
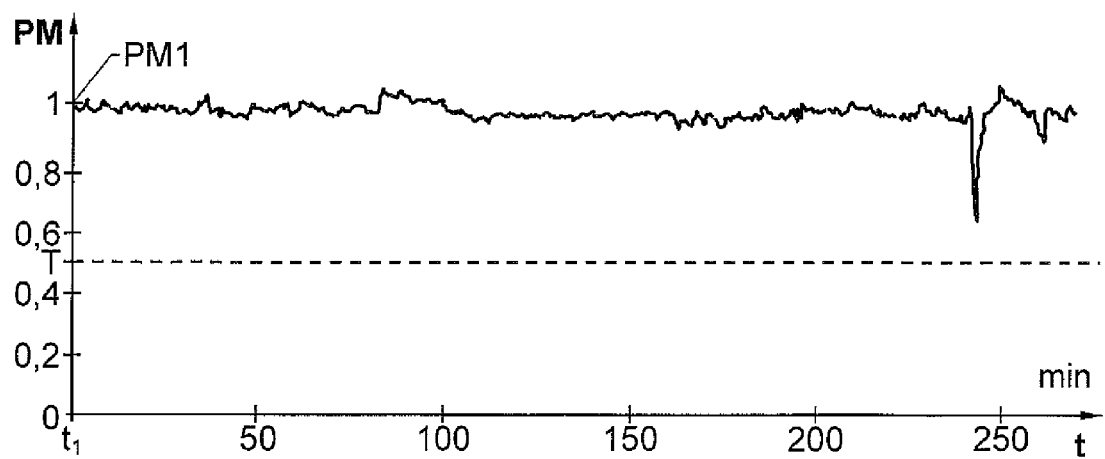
FIG. 3b shows a graph illustrating how the proposed pulse magnitude measure of the first subject varies over time.

FIG. 3b shows a graph, which illustrates the initial pulse magnitude measure PM1 in respect of a first subject being exposed to an extracorporeal blood treatment. Preferably, the initial pulse magnitude measure PM1 is not only derived from a singular pulse shape parameter $p_{PS}$, however from based on an average of a number of such parameters registered during an initial measurement period. The graph in FIG. 3b represents time t in minutes along the horizontal axis, and the pulse magnitude measure PM along the vertical axis.

According to the invention, the processing unit 128 may determine the pulse magnitude measure PM via one or more of the following strategies. For example, the difference between a maximum and a minimum value of the pulse shape parameter $p_{PS}$ registered during a pulse stroke can be calculated. Alternatively, the envelope of the pulse shape parameter $p_{PS}$ can be detected, e.g. by calculating the so-called Hilbert-transform. The root-mean-square (RMS) measure can also be utilized to determine the pulse magnitude measure PM based on the pulse shape parameter $p_{PS}$. Nevertheless, this requires a prior calibration of the parameter values to a zero average.

FIG. 3a shows a graph illustrating the first subject's systolic and diastolic blood pressure variations $BP_S$ and $BP_D$ respectively in mmHg during the treatment. The blood pressure BP varies throughout the treatment. However, as can be seen in FIG. 3b, no hypotension occurs. Apart from a dip around 245 minutes into the treatment, the pulse magnitude measure PM also remains relatively stable.

During a measurement period subsequent to the first instance $t_1$ (i.e. here from t=0 and onwards), the processing unit 128 is adapted to calculate a respective pulse magnitude measure PM based on each of a number of received pulse shape parameters $p_{PS}$. For each pulse magnitude measure PM in the measurement period, the processing unit 128 is further adapted to investigate whether or not the measure PM fulfills a decision criterion relative to the initial pulse magnitude measure PM1. If such a decision criterion is found to be fulfilled, the processing unit 128 is adapted to generate an alarm triggering signal α. The alarm triggering signal α, in turn, is presumed to cause an alarm A to be activated in an alarm unit 125 of the control unit 120 itself, and/or in an external unit receiving the alarm triggering signal α. The pulse magnitude measure PM and the decision criterion will be discussed in detail below with reference to FIGS. 4, 5 and 6.

Figure 2:
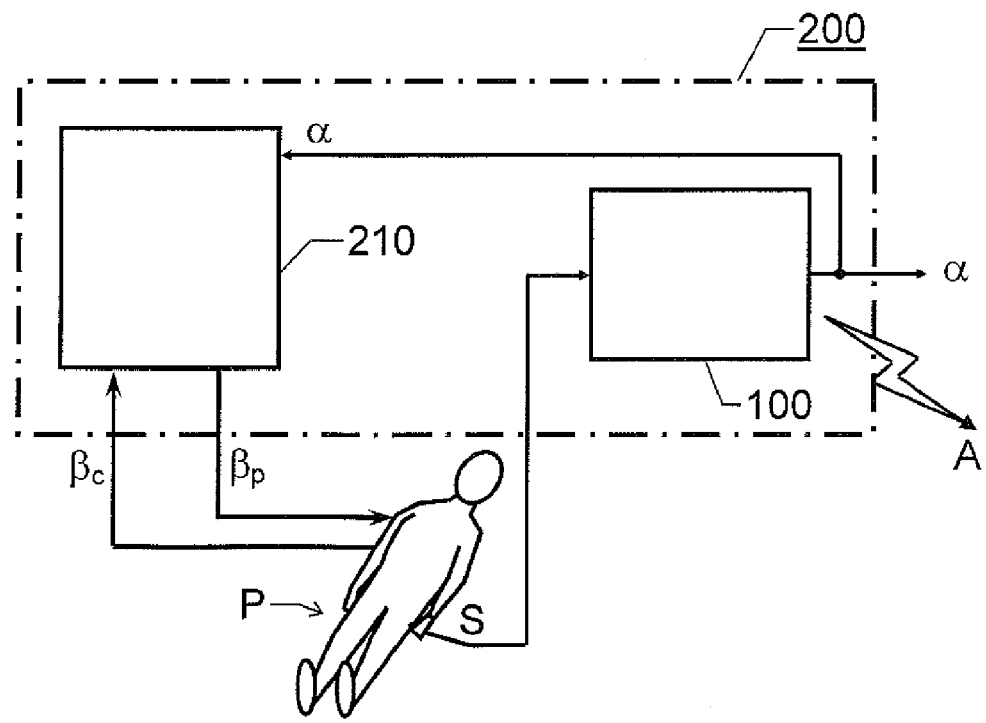
FIG. 2 shows a block diagram over a medical system according to one embodiment of the invention.

FIG. 2 shows a block diagram over a medical system 200 according to one embodiment of the invention for performing blood treatment of a subject P. To this aim the system 200 includes a dialysis machine 210, which may be adapted to perform extracorporeal blood treatment of the subject P, i.e. the machine 210 is adapted to extract contaminated blood $β_c$ from the subject P and return purified blood $β_p$ to the subject P. The system 200 also includes the above-described alarm arrangement 100 for predicting any rapid blood pressure decreases being potentially unhealthy to the subject P. Thus, in parallel with cleaning the subject's P blood, the alarm arrangement 100 monitors him/her regarding the risk that acute symptomatic hypotension occurs. In case of an alarm signal α, the overseeing staff can be informed and/or the dialysis machine 210 can be controlled to adjust its treatment parameter in order to avoid a hypotension situation. This type of adjustment is symbolized by means of a feedback signal α from the alarm arrangement 100 to the dialysis machine 210.

Preferably, the control unit 120 (see FIG. 1) in the arrangement 100 is adapted to predict rapid symptomatic blood pressure decrease in the subject P based on an initial pulse magnitude measure PM1 calculated from a pulse shape parameter $p_{PS}$ received during an initial phase of the blood treatment when the subject is still relatively unaffected by this treatment.

Figure 4A:
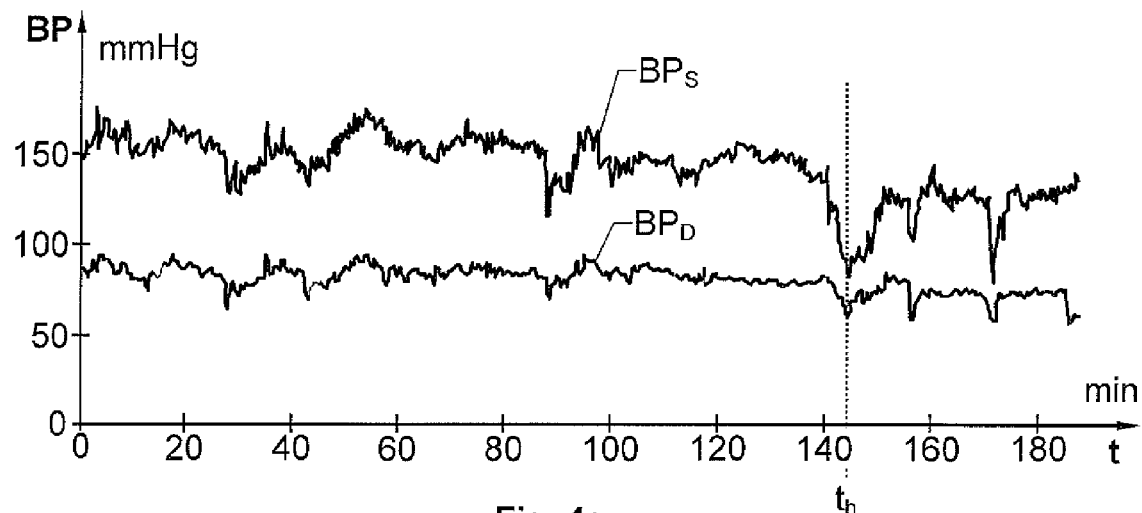
FIG. 4a shows a graph illustrating an example of a second subject's blood pressure variation during a blood treatment process.
Figure 5A:
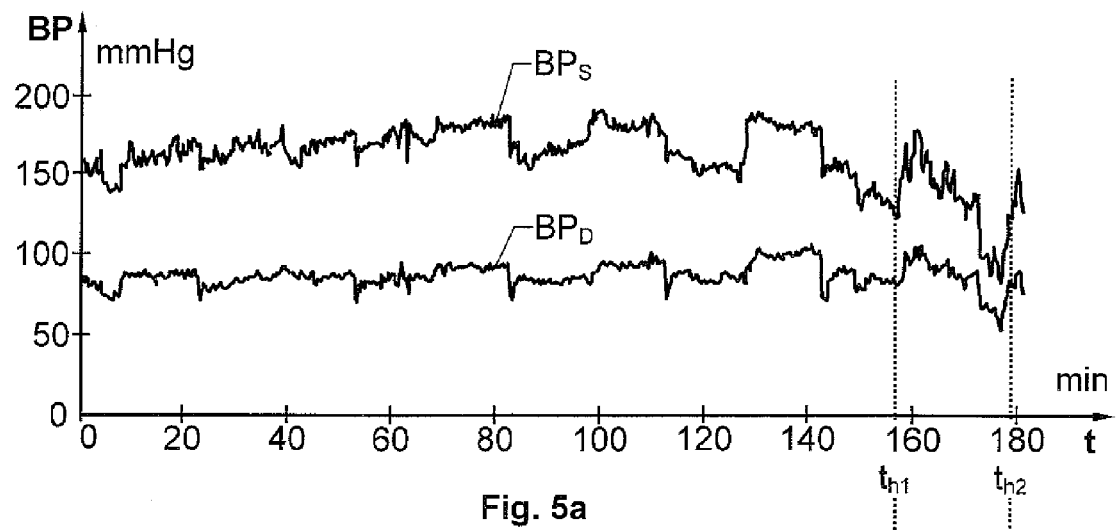
FIG. 5a shows a graph illustrating an example of a third subject's blood pressure variation during a blood treatment process.

Turning now to FIG. 4a, we see a diagram with a graph exemplifying how the systolic blood pressure $BP_S$ and the diastolic blood pressure $BP_D$ in mmHg of a second subject varies during an extracorporeal blood treatment. At a point in time $t_h$ around 145 minutes into the treatment, the subject suffers from acute symptomatic hypotension. This event is preceded by a rapid decrease BP in both the systolic $BP_S$ and diastolic $BP_D$ blood pressures.

Figure 4B:
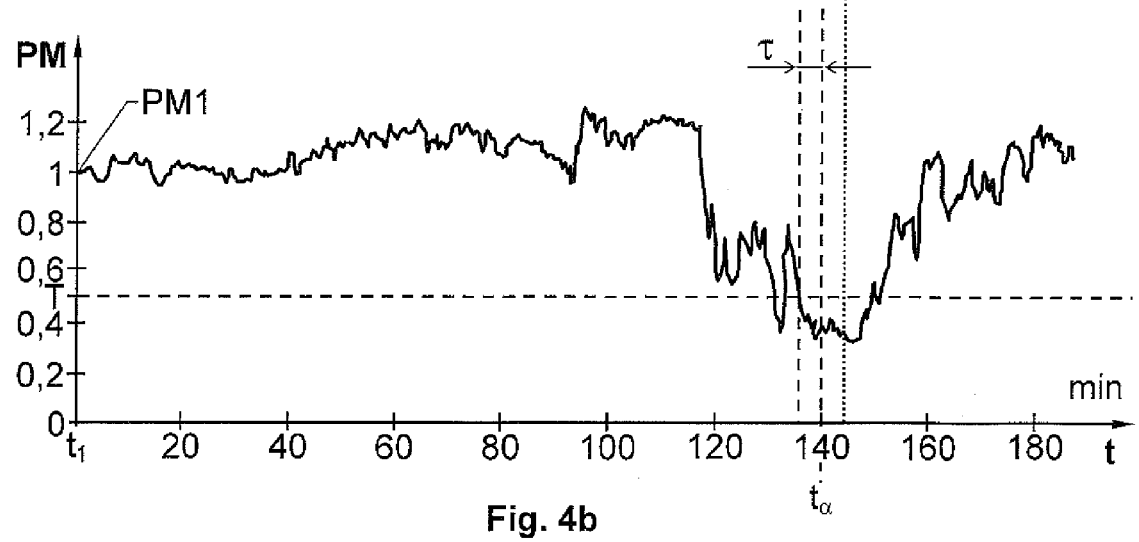
FIG. 4b shows a graph illustrating how the proposed pulse magnitude measure of the second subject varies over time.

Referring further to FIG. 4b, we will now explain how the proposed pulse magnitude measure PM and a threshold value T are calculated according to embodiments of the invention, and how evaluation of these parameters is used to predict the hypotension event.

The processing unit 128 of FIG. 1 is adapted to investigate whether a decision criterion is fulfilled with respect to the pulse shape parameters $p_{PS}$ received during the measurement period. In this example, the measurement period starts at t=0, and the period continues throughout the interval covered by the diagrams of FIGS. 4a and 4b.

The processing unit 128 of the control unit 120 preferably calculates the threshold value T as follows. First, the initial pulse magnitude measure PM1 derived at $t_1$ (i.e. here t=0) is normalized. In this example PM1=1, however technically, any other reference is conceivable. Then the normalized value is divided by a predefined denominator, which can be any number between 1.2 and 5, say 2. As a result, the threshold value T is obtained. Consequently, given that the predefined denominator is 2, T becomes 0.5 as is illustrated in FIG. 4b by means of a dashed line. In the measurement period after $t_1$, the processing unit 128 calculates a normalized pulse magnitude measur PM for each received pulse shape parameter $p_{PS}$ by dividing an original magnitude measure with the normalized initial pulse magnitude measure PM1 (that is derived from the pulse shape parameter $p_{PS}$ received at the first instance $t_1$). Hence, a pulse magnitude measure PM representing a larger pulse magnitude than that of the pulse shape parameter $p_{PS}$ received at the first instance $t_1$, results in a pulse magnitude measure PM>1, and conversely, a pulse magnitude measure PM representing a smaller pulse magnitude than that of the pulse shape parameter $p_{PS}$ received at the first instance $t_1$ results in a pulse magnitude measure PM<1.

When the pulse magnitude measure PM has been derived, the processing unit 128 regards the above-mentioned decision criterion to be fulfilled if:

(a) an examined pulse magnitude measure PM of a given pulse shape parameter is below the threshold value T; and (b) a predetermined amount of the pulse magnitude measures PM of the pulse shape parameters $p_{PS}$ received within a test period τ after the given pulse shape parameter are below the threshold value T.

According to one embodiment of the invention, the predetermined amount is a value representing approximately 50% to approximately 100% of the pulse magnitude measures PM of the pulse shape parameters $p_{PS}$ received within the test period τ. The predetermined amount may represent all the pulse magnitude measures PM of the pulse shape parameters $p_{PS}$ received within the test period τ. Nevertheless, to avoid interruption by singular pulse magnitude measures PM above the threshold value T, it can be advantageous to assign a predetermined amount equivalent to less than 100%. Alternatively, a secondary threshold value can be assigned somewhat above the threshold value T, and the processing unit 128 may employ a hysteresis algorithm, such that once the pulse magnitude measures PM has fallen below the threshold value T, the decision criterion is deemed fulfilled if, at expiry of the test period τ, the pulse magnitude measures PM has not exceeded the secondary threshold value.

In the example illustrated in FIG. 4b, the pulse magnitude measure PM for the first time falls below the threshold value T around t=128 minutes. Here, we assume that the above-mentioned predetermined amount is 100%, and that the test period τ is 5 minutes long. Hence, the test period τ ends around t=133 minutes. At this point in time, however, the pulse magnitude measure PM again exceeds the threshold value T. Therefore, no alarm triggering signal will be generated by the processing unit 128.

Around t=135 minutes, the pulse magnitude measure PM returns to a level below the threshold value T, and this time the pulse magnitude measure PM remains below the threshold value T for period exceeding the test period τ (here 5 minutes). Consequently, at the end of the test period τ (i.e. at approximately t=140 minutes), the processing unit generates the alarm triggering signal α. It is then around 5 minutes left until t=$t_h$ when hypotension occurred. Thus, aided by the alarm triggering signal α, it had been possible to perform appropriate, manual and/or automatic, hypotension inhibiting actions in due time. It is further advantageous if the processing unit 128 is adapted to generate an attention signal (e.g. causing a yellow lamp on the unit to be lit up) whenever the pulse magnitude measure PM is below the threshold value T. Thus, any supervising staff can obtain an earliest possible indication of that acute symptomatic hypotension may be forthcoming, and that therefore the subject needs extra attention. If, at the end of the pulse magnitude measure PM rises above the threshold value T without the decision criterion having been fulfilled, the attention signal is deactivated.

Of course, according to the invention, a test period τ length other than five minutes is likewise conceivable. In fact, the test period τ may represent any interval selected from a range extending from approximately three minutes to approximately fifteen minutes. The length of the test period τ is a design parameter that is selected to attain a desired balance between robustness and reliability. Preferably, the choice of the test period τ is made conjoint with the predefined denominator above. Namely, for a given balance between early hypotension warning and false alarms, a relatively large denominator requires a comparatively short test period, and vice versa.

Moreover, if in the example of FIG. 4b, the predetermined amount of pulse magnitude measure PM below the threshold value T required to fulfill the decision criterion had been selected to a value less than 100%, say 60%, the alarm triggering signal α would have been generated already at expiry of the first test period τ (i.e. around t=133 minutes).

Analogous to FIGS. 4a and 4b, FIGS. 5a and 5b show graphs exemplifying a third subject's blood pressure variation during an extracorporeal blood treatment and a corresponding pulse magnitude measure variation respectively.

In this example, the subject suffers from two acute symptomatic hypotension events at t=$t_{h1}$ (around 155 minutes into the treatment) and at t=$t_{h2}$ (around 178 minutes into the treatment) respectively. To facilitate comparison with the previous examples, we have also here chosen to normalize the initial pulse magnitude measure PM1 derived at $t_1$ (t=0) to 1, selected a threshold value T=0.5 (i.e. the predefined denominator is 2), and set the length of the test period T to five minutes. Furthermore, we regard the decision criterion as fulfilled if all pulse magnitude measures PM of the pulse shape parameters pPS received within the test period T fall below the threshold value T.

Figure 5B:
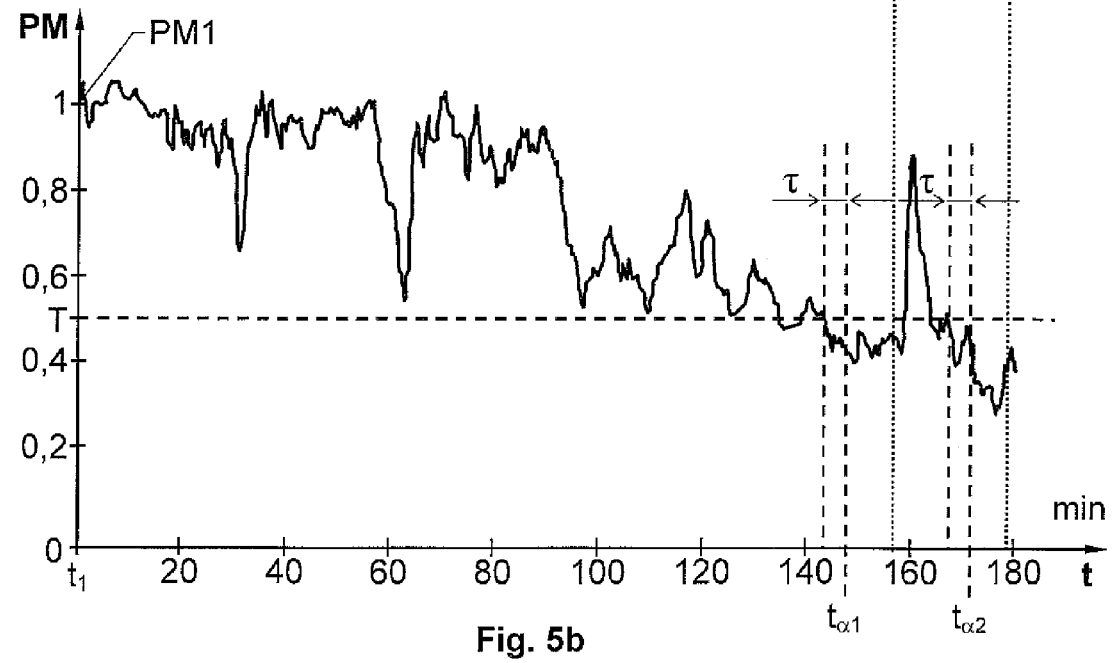
FIG. 5b shows a graph illustrating how the proposed pulse magnitude measure of the third subject varies over time.

As is apparent from the diagram in FIG. 5b, given these parameter values, the processing unit 128 will generate the alarm triggering signal α at t=$t_{α1}$ (around 145 minutes into the treatment) and at t=$t_{α2}$ (around 171 minutes into the treatment) respectively. Thus approximately seven to ten minutes advance indications of the upcoming hypotension events are provided.

Returning briefly to FIG. 3b, we see that the pulse magnitude measure PM here never falls below the threshold value T (here 0.5). Thus, in this case, the processing unit 128 will not generate any alarm triggering signal α.

We now return to FIG. 1. According to one embodiment of the invention, the arrangement 100 includes an auxiliary recording means 130 adapted to repeatedly register a bio-impedance parameter $p_{B1}$ that represents a degree of contraction of the subject's P capillary blood vessels. In this embodiment, the processing unit 128 is further adapted to receive this bio-impedance parameter $p_{B1}$, and investigate whether or not the parameter $p_{B1}$ fulfills an auxiliary alarm criterion. If this criterion is found to be fulfilled, the processing unit 128 is adapted to generate the alarm triggering signal α. Hence, the performance and reliability of the arrangement 100 is improved. To further improve the usability of the arrangement 100, it is preferable if the auxiliary recording means 130 is adapted to determine a bio-impedance parameter being essentially unrelated to the contraction of the subject's P capillary blood vessels. Thus, the auxiliary recording means 130 may register an absolute body temperature, variations in the body temperature and/or an amount of sweat on the subject P, and the processing unit may be adapted to test the auxiliary alarm criterion against one or more of these parameters.

Figure 6:
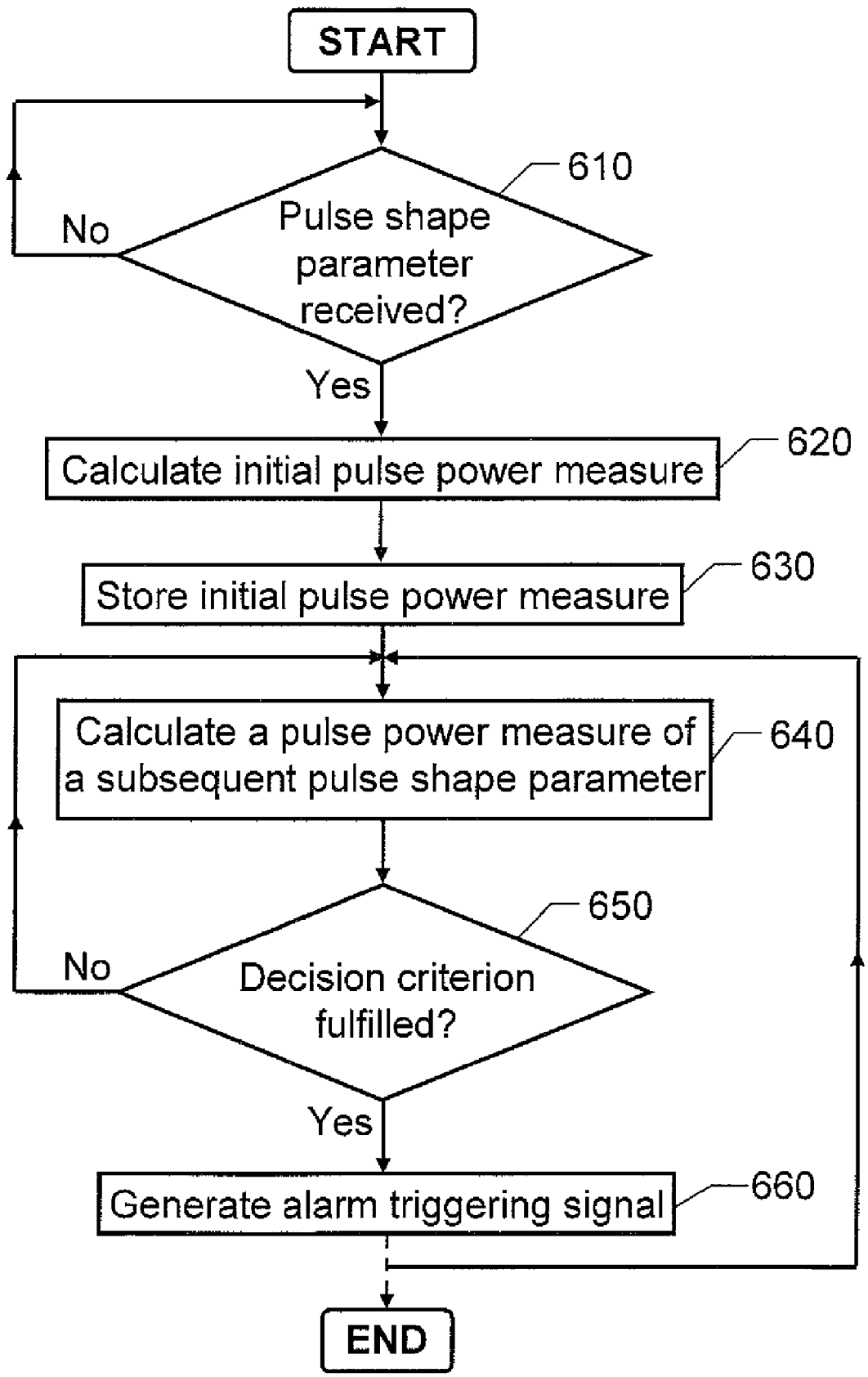
FIG. 6 shows a flow diagram which illustrates the general method of predicting rapid symptomatic blood pressure decrease according to the invention.

In order to sum up, the general method of predicting rapid symptomatic blood pressure decrease in a subject according to the invention will be described below with reference to the flow diagram in FIG. 6.

A first step 610 investigates whether or not a pulse shape parameter in respect of a peripheral body part of the subject has been received. If no such parameter has been received, the procedure loops back and stays in the step 610. If, however, a pulse shape parameter is received, a step 620 follows, which calculates an initial pulse magnitude measure based on a pulse shape parameter received at a first instance. It is here presumed that the pulse shape parameter has been registered by means of a pulse oximetry measurement wherein the pulse shape parameter is determined based on light absorption variations in at least one blood vessel of the subject.

A following step 630, stores the initial pulse magnitude measure in a memory means. Thereafter, a measurement period follows during which a step 640 calculates a respective pulse magnitude measure based on each received pulse shape parameter. Moreover, for each pulse magnitude measure in the measurement period, a step 650 subsequent to the step 640, investigates whether or not the pulse magnitude measure fulfills a decision criterion relative to the initial pulse magnitude measure. If the decision criterion is found not to be fulfilled, and provided that the measurement period still is active, the procedure loops back to the step 640.

However, if in the step 650 it is found that the decision criterion is fulfilled, a step 660 follows, which causes an alarm triggering signal to be generated. Thereafter, the procedure may either end, or loop back to the step 640 (provided that the measurement period still is active). Preferably, the measurement period is inactivated in response to a manual intervention, such as depressing a reset button. Namely, thereby it is straightforward to resume (or actually maintain) the measurement period even in cases where the measurement may have been involuntary interrupted, for instance due to that the sensor unit 115 has fallen off the subject P. In such cases, the sensor unit 115 may simply be reattached, where after the measurement continues.

All of the process steps, as well as any sub-sequence of steps, described with reference to the FIG. 6 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code; object code, a code intermediate source and object code such as in partially compiled form, or in any other form suitable for use in the implementation of the process according to the invention. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. An alarm arrangement, comprising:
   a pulse recording device configured to repeatedly register a pulse shape parameter in a peripheral body part of a subject, said pulse recording device having a pulse oximetry instrument configured to register the pulse shape parameter based on light response variations in at least one blood vessel of the subject; and
   a control unit configured to receive the pulse shape parameter and investigate whether the pulse shape parameter fulfills an alarm criterion, wherein if said alarm criterion is fulfilled, said control unit causes an alarm to be activated, said control unit having a processing unit configured to:
      calculate an initial pulse magnitude measure based on a pulse shape parameter received at a first instance;
      store the initial pulse magnitude measure in a memory means associated with the control unit;
      calculate, during a measurement period subsequent to the first instance, a respective pulse magnitude measure based on each of a number of received pulse shape parameters; and
      investigate, for each pulse magnitude measure in the measurement period, whether the pulse magnitude measure fulfills a decision criterion relative to the initial pulse magnitude measure, and wherein said decision criterion is fulfilled, said processing unit is further configured to generate an alarm triggering signal.

2. The arrangement according to claim 1, wherein the processing unit is configured to regard the decision criterion as fulfilled if:
   an examined pulse magnitude measure of a given pulse shape parameter is below a threshold value calculated based on the initial pulse magnitude measure; and
   a predetermined amount of the pulse magnitude measures of the pulse shape parameters, received within a test period after the registering of the given pulse shape parameter, are below the threshold value.

3. The arrangement according to claim 2, wherein the predetermined amount is a value representing approximately 50% to approximately 100% of the pulse magnitude measures of the pulse shape parameters received within the test period.

4. The arrangement according to claim 2, wherein the predetermined amount represents all the pulse magnitude measures of the pulse shape parameters received within the test period.

5. The arrangement according to claim 2, wherein the test period is an interval selected from a range extending from approximately three minutes to approximately fifteen minutes.

6. The arrangement according to claim 5, wherein the test period is approximately five minutes long.

7. The arrangement according to claim 2, wherein the processing unit is configured to calculate the threshold value by:
   normalizing the initial pulse magnitude measure; and
   dividing the normalized initial pulse magnitude measure by a predefined denominator.

8. The arrangement according to claim 7, wherein the processing unit is configured to, during the measurement period, calculate a pulse magnitude measure for a received pulse shape parameter by dividing an original measure with the initial pulse magnitude measure.

9. The arrangement according to claim 8, wherein the predefined denominator is a value selected from a range extending from approximately 1.2 to approximately 5.

10. The arrangement according to claim 1, wherein the arrangement comprises:
    an auxiliary recording means configured to repeatedly register a bio-impedance parameter representing a degree of contraction of the subject's capillary blood vessels, and
    the processing unit is further configured to receive the bio-impedance parameter, investigate whether the bio-impedance parameter fulfills an auxiliary alarm criterion, and generate the alarm triggering signal if the auxiliary alarm criterion is fulfilled.

11. The arrangement according to claim 1, wherein the arrangement is configured to predict rapid symptomatic blood pressure decrease in a subject undergoing blood treatment, and the processing unit is configured to calculate the initial pulse magnitude measure based on a pulse shape parameter received during an initial phase of the blood treatment.

12. A medical system configured to perform blood treatment of a subject, wherein the system comprises:
    a dialysis machine configured to perform extracorporeal blood treatment of the subject; and
    the alarm arrangement according to claim 1.

13. A method, comprising:
- registering a pulse shape parameter in respect of a peripheral body part of a subject at repeated occasions,
- investigating, for each pulse shape parameter, whether the pulse shape parameter fulfills an alarm criterion, and if the alarm criterion is fulfilled;
- causing an alarm to be activated, wherein the registering of the pulse shape parameter involves a pulse oximetry measurement, said pulse shape parameter being determined based on light response variations in at least one blood vessel of the subject, and the method further comprising:
  - calculating an initial pulse magnitude measure based on a pulse shape parameter received at a first instance;
  - storing the initial pulse magnitude measure in a memory means; calculating, during a measurement period subsequent to the first instance, a respective pulse magnitude measure based on each of a number of received pulse shape parameters;
  - investigating, for each pulse magnitude measure in the measurement period, whether the measure fulfills a decision criterion relative to the initial pulse magnitude measure, and if the decision criterion is fulfilled;
  - generating an alarm triggering signal.

14. The method according to claim 13, wherein the decision criterion being fulfilled if:
- an examined pulse magnitude measure of a given pulse shape parameter is below a threshold value calculated based on the initial pulse magnitude measure; and
- a predetermined amount of the pulse magnitude measures of the pulse shape parameters, received within a test period after the registering of the given pulse shape parameter, are below the threshold value.

15. The method according to claim 14, wherein the predetermined amount is a value representing approximately 50% to approximately 100% of the pulse magnitude measures of the pulse shape parameters received within the test period.

16. The method according to claim 14, wherein the predetermined amount representing all the pulse magnitude measures of the pulse shape parameters received within the test period.

17. The method according to claim 14, wherein the test period is an interval selected from a range extending from approximately three minutes to approximately fifteen minutes.

18. The method according to claim 17, wherein the test period is approximately five minutes long.

19. The method according to claim 14, wherein the threshold value is calculated by:
- normalizing the initial pulse magnitude measure, and
- dividing the normalized initial pulse magnitude measure by a predefined denominator.

20. The method according to claim 19, wherein, during the measurement period, a pulse magnitude measure is calculated for a received pulse shape parameter by dividing an original measure with the initial pulse magnitude measure.

21. The method according to claim 20, wherein the predefined denominator being a value selected from a range extending from approximately 1.2 to approximately 5.

22. The method according to claim 13, further comprising:
- registering a bio-impedance parameter representing a degree of contraction of the subject's capillary blood vessels at repeated occasions; and
- investigating whether the bio-impedance parameter fulfills an auxiliary alarm criterion, and if the auxiliary alarm criterion is fulfilled;
- generating the alarm triggering signal.

23. A computer program directly loadable into the internal memory of a computer, comprising software for controlling the steps of claim 13 when said program is run on the computer.

24. A computer readable medium, having a program recorded thereon, where the program is to make a computer control the steps of claim 13.

* * * * *